United States Patent
Kinsley et al.

(10) Patent No.: US 10,772,571 B2
(45) Date of Patent: Sep. 15, 2020

(54) METHOD AND SYSTEMS FOR CORRECTING FOR ARTERIAL COMPLIANCE IN A BLOOD PRESSURE ASSESSMENT

(71) Applicant: Wech Allyn, Inc., Skaneateles Falls, NY (US)

(72) Inventors: Matthew J. Kinsley, Marcellus, NY (US); David E. Quinn, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 952 days.

(21) Appl. No.: 15/371,444

(22) Filed: Dec. 7, 2016

(65) Prior Publication Data
US 2018/0132796 A1     May 17, 2018

Related U.S. Application Data

(60) Provisional application No. 62/422,280, filed on Nov. 15, 2016.

(51) Int. Cl.
| | |
|---|---|
| *A61B 5/00* | (2006.01) |
| *A61B 5/022* | (2006.01) |
| *A61B 5/02* | (2006.01) |

(52) U.S. Cl.
CPC ............ *A61B 5/7278* (2013.01); *A61B 5/022* (2013.01); *A61B 5/742* (2013.01); *A61B 5/02007* (2013.01);
(Continued)

(58) Field of Classification Search
None
See application file for complete search history.

(56) References Cited

U.S. PATENT DOCUMENTS

| | | |
|---|---|---|
| 5,027,641 A | 7/1991 | Costello, Jr. |
| 5,103,833 A | 4/1992 | Apple |
| (Continued) | | |

FOREIGN PATENT DOCUMENTS

| | | |
|---|---|---|
| CN | 1345571 A | 9/2000 |
| CN | 101589949 B | 5/2012 |
| (Continued) | | |

OTHER PUBLICATIONS

Arterial Pulse Power Analysis: The LiDCO™ plus System; A. Rhodes and R. Sunderland; Oct. 21, 2016.
(Continued)

*Primary Examiner* — Kaylee R Wilson
*Assistant Examiner* — Jay B Shah
(74) *Attorney, Agent, or Firm* — Kenneth C. Baran

(57) ABSTRACT

A system for monitoring blood pressure of a subject includes a primary system for determining a first blood pressure and a corrective system. The corrective system includes a cuff configured to be operated in an inflation phase and a deflation phase, a sensor array which produces inflation and deflation phase output signals, and a processor. The processor is configured to a) determine first and second output values from the inflation phase output signal and b) determine third and fourth output values from the deflation phase output signal. The processor is also configured to determine a correction applicable to the first blood pressure. The correction is a function of the first, second, third and fourth output values.

32 Claims, 13 Drawing Sheets

(52) U.S. Cl.
CPC ..... *A61B 5/7203* (2013.01); *A61B 2560/0223* (2013.01)

(56) References Cited

U.S. PATENT DOCUMENTS

| | | | |
|---|---|---|---|
| 5,218,968 | A | 6/1993 | Apple |
| 5,303,977 | A | 4/1994 | Sereboff |
| 5,311,872 | A | 5/1994 | Apple |
| 5,417,220 | A | 5/1995 | Apple |
| 5,423,322 | A | 6/1995 | Clark et al. |
| 5,447,163 | A | 9/1995 | Apple |
| 5,533,511 | A | 7/1996 | Kaspari et al. |
| 5,577,508 | A | 11/1996 | Medero |
| 5,579,776 | A | 12/1996 | Medero |
| 5,590,662 | A | 1/1997 | Hersh et al. |
| 5,651,370 | A | 7/1997 | Hersh et al. |
| 5,680,870 | A | 10/1997 | Hood, Jr. et al. |
| 5,724,981 | A | 3/1998 | Apple |
| 5,913,826 | A | 6/1999 | Blank |
| 5,993,396 | A | 11/1999 | Friedman et al. |
| 6,050,951 | A | 4/2000 | Friedman et al. |
| 6,358,213 | B1 | 3/2002 | Friedman et al. |
| 6,440,080 | B1 | 8/2002 | Booth et al. |
| 6,475,154 | B1 | 11/2002 | Wu et al. |
| 6,517,495 | B1 | 2/2003 | Hersh |
| 6,733,461 | B2 | 5/2004 | Bratteli |
| 6,767,328 | B2 | 7/2004 | Kulik |
| 7,070,566 | B2 | 7/2006 | Medero et al. |
| 7,153,269 | B1 | 12/2006 | Blansett |
| 7,186,218 | B2 | 3/2007 | Hersh et al. |
| 7,226,421 | B1 | 6/2007 | Hersh et al. |
| 7,300,404 | B1 | 11/2007 | Kolluri et al. |
| 7,390,302 | B2 | 6/2008 | Friedman et al. |
| 7,462,152 | B2 | 12/2008 | Kolluri et al. |
| 7,544,167 | B2 | 6/2009 | Hersh et al. |
| 7,678,059 | B2 | 3/2010 | Friedman et al. |
| 7,775,987 | B2 | 8/2010 | Hersh et al. |
| 8,016,765 | B2 | 9/2011 | Ramsey |
| 8,047,998 | B2 | 11/2011 | Kolluri et al. |
| 8,133,184 | B2 | 3/2012 | Williams et al. |
| 8,197,414 | B2 | 6/2012 | Quinn et al. |
| 8,211,030 | B2 * | 7/2012 | Donehoo ............... A61B 5/022 600/485 |
| 8,239,010 | B2 | 8/2012 | Banet et al. |
| 8,308,647 | B2 | 11/2012 | Kolluri et al. |
| 8,419,649 | B2 | 4/2013 | Banet et al. |
| 8,556,821 | B2 | 10/2013 | Hersh et al. |
| 8,574,161 | B2 | 11/2013 | Banet et al. |
| 8,602,997 | B2 | 12/2013 | Banet et al. |
| 8,721,557 | B2 | 5/2014 | Chen et al. |
| 8,740,802 | B2 | 6/2014 | Banet et al. |
| 8,740,803 | B2 | 6/2014 | Hersh et al. |
| 8,808,188 | B2 | 8/2014 | Banet et al. |
| 8,840,561 | B2 | 9/2014 | Lane et al. |
| 9,022,942 | B2 | 5/2015 | Quinn et al. |
| 9,072,433 | B2 | 7/2015 | Chen et al. |
| 9,161,700 | B2 | 10/2015 | Banet et al. |
| 9,215,986 | B2 | 12/2015 | Banet et al. |
| 2004/0167413 | A1 | 8/2004 | Bratteli |
| 2007/0016083 | A1 | 1/2007 | Hasegawa |
| 2008/0221461 | A1 | 9/2008 | Zhou et al. |
| 2008/0235058 | A1 | 9/2008 | Friedman et al. |
| 2008/0243009 | A1 | 10/2008 | Hersh et al. |
| 2009/0118628 | A1 | 5/2009 | Zhou et al. |
| 2010/0160797 | A1 | 6/2010 | Banet et al. |
| 2010/0174202 | A1 | 7/2010 | Hersh et al. |
| 2011/0025944 | A1 | 2/2011 | Lee et al. |
| 2011/0066043 | A1 | 3/2011 | Banet et al. |
| 2012/0149994 | A1 | 6/2012 | Luczyk et al. |
| 2012/0157791 | A1 | 6/2012 | Hersh |
| 2012/0209129 | A1 | 8/2012 | Smith et al. |
| 2012/0283583 | A1 | 11/2012 | Batkin et al. |
| 2014/0066793 | A1 | 3/2014 | Mukkamala et al. |
| 2014/0135634 | A1 | 5/2014 | Pranevicius et al. |
| 2014/0142445 | A1 | 5/2014 | Banet et al. |
| 2014/0180144 | A1 | 6/2014 | Chen et al. |
| 2014/0276145 | A1 | 9/2014 | Banet et al. |
| 2014/0364748 | A1 | 12/2014 | Lane et al. |
| 2015/0032012 | A1 | 1/2015 | Marinello et al. |
| 2015/0045679 | A1 | 2/2015 | St. Pierre et al. |
| 2015/0282721 | A1 | 10/2015 | Chen et al. |
| 2015/0327785 | A1 | 11/2015 | Lading et al. |
| 2016/0045119 | A1 | 2/2016 | David et al. |
| 2016/0143546 | A1 | 5/2016 | Mccombie et al. |
| 2016/0220195 | A1 | 8/2016 | Abu-Tarif et al. |

FOREIGN PATENT DOCUMENTS

| | | |
|---|---|---|
| JP | 2003180640 A | 7/2003 |
| WO | 2016081519 A1 | 5/2016 |
| WO | 2016126445 A1 | 8/2016 |

OTHER PUBLICATIONS

Oscillometric measurement of systolic and diastolic blood pressures validated in a physiologic mathematical model; charles F. Babbs; BioMedical Engineering OnLine 2012, 11:56; BioMed Central.

Cardiac Output Monitoring by Long Time Interval Analysis of a Radial Arterial Blood Pressure Waveform with Correction for Arterial Compliance Changes using Pulse Transit Time; Moshen Moslehpour, Guanqun Zhang, and Ramakrishna Mukkamala, Member, IEEE; 33rd Annual International Conference of the IEEE EMBS, Boston, Massachusetts, USA, Aug. 30-Sep. 3, 2011.

Clinical evaluation of the Welch Allyn SureBP algorithm for automated blood pressure measurement; Bruce S. Alpert; Devices and technology; Blood Pressure Monitoring 2007, vol. 12 No. 4.

Mechanism of Cuff-Less Blood Pressure Measurement Using MMSB; Yibin Li, Yangyu Gao, Ning Deng; Institute of Microelectronics, Tsinghua University, Beijing, 100084, China; Scientific Research; Engineering, 2013, 5, 123-125.

International Search Report for PCT/US2017/061725; Date of the actual completion of the international search—Feb. 6, 2018;Date of mailing of the international search report—dated Feb. 7, 2018; Authorized officer—Kim, Yeonkyung.

Written Opinion of the International Searching Authority for PCT/US2017/061725; Date of completion of this opinion—Feb. 6, 2018; Date of mailing—dated Feb. 7, 2018; Authorized officer—Kim, Yeonkyung.

* cited by examiner

METHOD AND SYSTEMS FOR CORRECTING FOR ARTERIAL COMPLIANCE IN A BLOOD PRESSURE ASSESSMENT

TECHNICAL FIELD

The subject matter described herein relates to accounting for the effects of arterial compliance when determining blood pressure.

BACKGROUND

Several techniques are known for noninvasively determining the blood pressure of a subject. Among these is an ausculcatory method in which a cuff is wrapped around a portion of the subject's body, usually the upper arm. The cuff is inflated with air thereby pressurizing the cuff so that the cuff compresses the subject's arm and occludes the artery extending therethrough. After the artery has been occluded, the pressure in the cuff is released in a controlled fashion. During the decompression a caregiver, aided by a stethoscope, listens for sounds known as Korotkov sounds, also referred to as K-sounds. Variations in the character of the K-sounds are used to discern the time of the post-occlusion initial onset of blood flow through the artery and the subsequent re-establishment of substantially normal blood flow through the artery. The cuff pressure at the onset of blood flow and at the re-establishment of normal blood flow are taken to be the subject's systolic and diastolic blood pressure values respectively.

A similar ausculcatory method relies on a microphone in the cuff rather than a caregiver listening for the K-sounds. An algorithm executed by a processor identifies the K-sounds and the associated systolic and diastiolic pressures.

Another method is an oscillometric method. The oscillometric method is similar to the microphone assisted ausculcatory method except that instead of using a microphone the cuff includes a pressure transducer, and instead of relying on the K-sounds as described above, the oscillometric technique relies on oscillations in the subject's blood pressure, that create relatively small disturbances in the cuff pressure, to identify the subject's systolic and diastolic blood pressure. The oscillations appear during the inflation phase of the oscillometric method, increase in amplitude to a peak amplitude with increasing cuff pressure, and then decrease in amplitude and vanish with further increases in cuff pressure. Similar oscillations appear during the deflation phase of the oscillometric method. The oscillations increase in amplitude to a peak amplitude with decreasing cuff pressure, and finally vanish with further decreases in cuff pressure. The amplitude of the oscillations is alternatively referred to as pulse height. The peak amplitude or pulse height is typically about 1 to 3 mm Hg. A graph of pulse height vs. cuff pressure is referred to as the pulse envelope. The pulse envelope has an ascending side corresponding to the pulses of increasing amplitude and a descending side corresponding to the pulses of decreasing amplitude. A processor analyzes the pulse envelope and takes the cuff pressure corresponding to the peak pulse height as an estimate of the subject's mean arterial pressure (MAP). The processor equates the subject's systolic blood pressure to the cuff pressure on the ascending side of the pulse envelope at a predefined fraction (less than 1.0) of the peak pulse amplitude. The processor equates the subject's diastolic blood pressure to the cuff pressure on the descending side of the pulse envelope at a predetermined fraction (also less than 1.0) of the peak pulse amplitude. The predefined and predetermined fractions may or may not be equal to each other.

Blood pressure may also be determined by way of cuffless techniques. One cuffless technique measures pulse transit time (PTT). PTT is the time it takes a pulse wave to propagate from a more upstream location to a more downstream location in a subject's artery. PTT is considered to be a good indication of MAP. A processor executes an algorithm to determine systolic and diastolic pressure from the MAP.

Although the foregoing techniques are widely used, they either do not account for the effects of arterial compliance on the blood pressure determination, or do not do so satisfactorily. Accordingly, the subject matter described herein discloses a system for correcting a blood pressure value to account for arterial compliance, a system for determining a blood pressure including a correction for arterial compliance, and a method of determining the correction.

SUMMARY

A system for monitoring blood pressure of a subject includes a primary system for determining a first blood pressure and a corrective system. The corrective system includes a cuff configured to be operated in 1) an inflation phase to at least partially occlude an artery of the subject and 2) a deflation phase. The corrective system also includes a sensor array configured to A) receive an inflation phase input signal associated with the occluded artery, B) generate an inflation phase output signal based on the received inflation phase signal, C) receive a deflation phase input signal associated with the artery, and D) generate a deflation phase output signal based on the received deflation phase signal. The blood pressure monitoring system also includes a processor configured to a) receive the inflation phase output signal and determine therefrom first and second output values, b) receive the deflation phase output signal and determine therefrom third and fourth output values, and c) determine a correction applicable to the first blood pressure. The correction is a function of the first, second, third and fourth output values.

A system for correcting a first blood pressure value of a subject includes a cuff configured to be operated in 1) an inflation phase to at least partially occlude an artery of the subject and 2) a deflation phase. The system also includes a sensor array, which can be one or more sensors. The sensor array is configured to A) receive an inflation phase input signal associated with the at least partially occluded artery, B) generate an inflation phase output signal based on the received inflation phase signal, C) receive a deflation phase signal associated with the artery, and D) generate a deflation phase output signal based on the received deflation phase signal. The system also includes a processor configured to a) receive the inflation phase output signal and determine therefrom first and second output values, b) receive the deflation phase output signal and determine therefrom third and fourth output values, and c) determine a correction as a function of the first, second, third and fourth output values.

A method of determining a correction to the blood pressure of a subject includes the steps of:
1. applying compression to an artery of the subject, thereby generating an inflation phase output signal. The applied compression is sufficient to at least partially occlude the artery;

2. determining, from the inflation phase output signal, a first intra-arterial pressure and a second intra-arterial pressure associated with a compression phase pulse envelope;
3. releasing the compression applied to the artery thereby generating a deflation phase output signal;
4. determining, from the deflation phase output signal, a third intra-arterial pressure and a fourth intra-arterial pressure associated with a decompression phase pulse envelope; and
5. establishing a correction as a function of the first, second, third, and fourth intra-arterial pressures.

BRIEF DESCRIPTION OF THE DRAWINGS

The foregoing and other features of the various embodiments of the system and method described herein will become more apparent from the following detailed description and the accompanying drawings in which.

DETAILED DESCRIPTION

Figure 1:
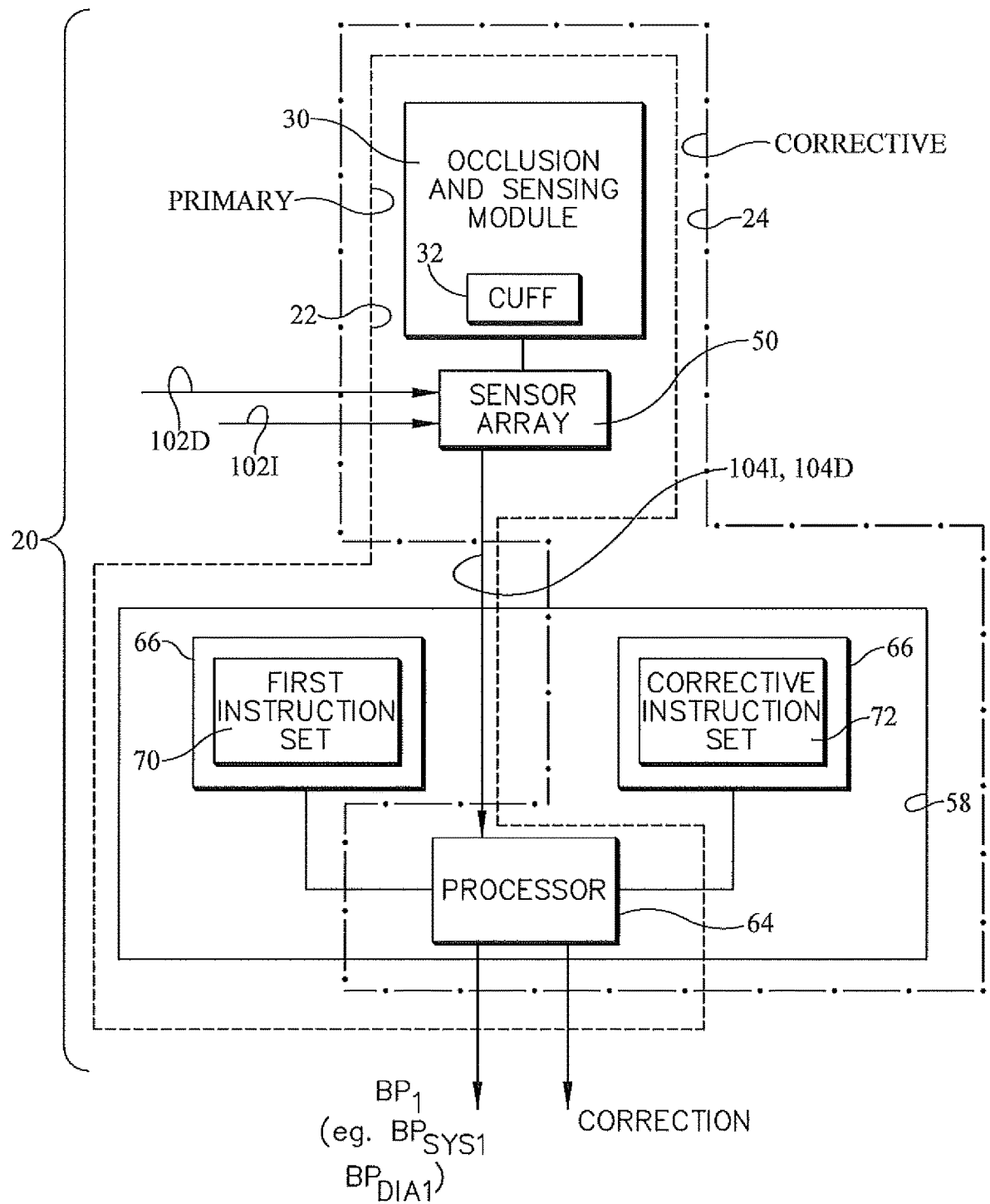
FIG. 1 is a diagram of the architecture of a blood pressure monitoring system which includes an oscillometric primary system and an oscillometric corrective system and in which the primary and corrective systems share a sensor array.

Reference will now be made to embodiments of the invention, examples of which are illustrated in the accompanying drawings. Features similar to or the same as features already described may be identified by the same reference numerals already used. The terms "substantially" and "about" may be used herein to represent the inherent degree of uncertainty that may be attributed to any quantitative comparison, value, measurement or other representation. These terms are also used herein to represent the degree by which a quantitative representation may vary from a stated reference without resulting in a change in the basic function of the subject matter at issue.

In the accompanying description and claims, the terms "occlude", "occlusion" and variations thereof include partial occlusion of an artery, at least insofar as partial occlusion produces the sought-after effects such as Korotkov sounds and the presence of pressure oscillations corresponding to an oscillometric pulse envelope.

Referring to FIG. 1 a system 20 for monitoring the blood pressure of a subject includes a primary system 22 (enclosed within a dashed border) for determining a first blood pressure and a corrective system 24 (enclosed within a dash-dot border). The corrective system establishes a correction which can be applied to the first blood pressure to account for the effects of arterial compliance. As will be explained in more detail below, the primary and corrective systems may have certain elements in common. The blood pressure monitoring system of FIG. 1 is referred to an oscillometric/oscillometric system (abbreviated O/O) because both the primary system 22 and the corrective system 24 employ an oscillometric technique.

Figure 2:
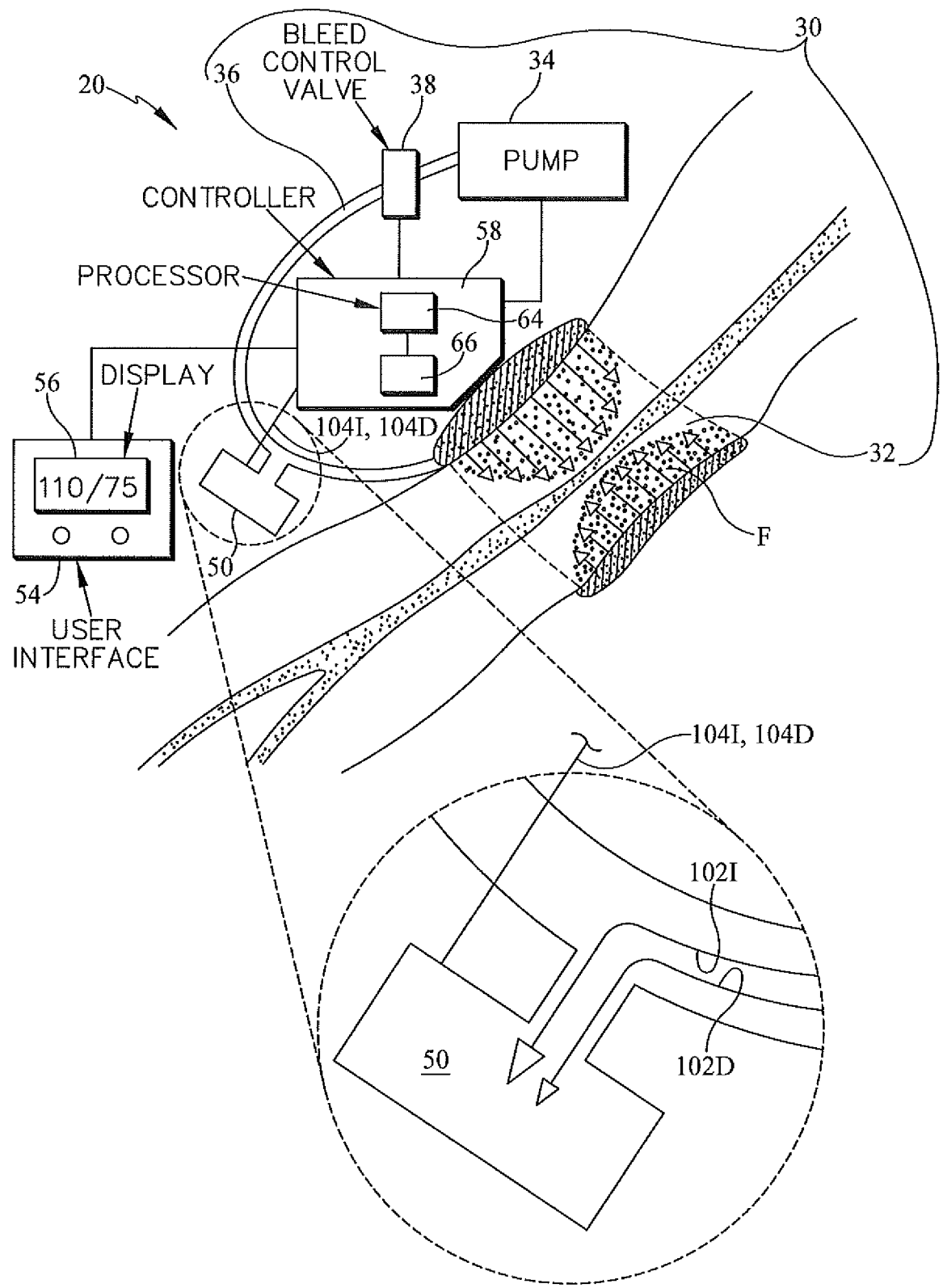
FIG. 2 is a view showing a subject's arm, an artery extending therethrough, and various elements of a blood pressure monitoring system.

Referring additionally to FIG. 2, corrective system 24 includes an occlusion and sensing module 30 comprising a cuff 32, shown wrapped around the subject's arm, a pump 34 for inflating the cuff, a tube 36 extending from the pump to the cuff, and a bleed control valve 38 in the tube for deflating the cuff. The corrective system includes a sensor array comprising one or more sensors or transducers. In the illustrated embodiment, the sensor array is a single pressure sensor 50 such as a piezo-resistive sensor which converts an applied pressure to an electrical signal. The cuff is configured to be operable in an inflation phase to compress and occlude an artery of the subject and in a deflation phase which gradually releases the compression on the artery and allows the artery to return to its decompressed, non-occluded, normally functioning state. The system also includes a user interface 54 with a display 56, and a controller 58 which includes a processor 64. A memory 66 contains a set of instructions including a first instruction set 70 associated with primary system 22 and a corrective instruction set 72 associated with corrective system 24.

Figure 3A:
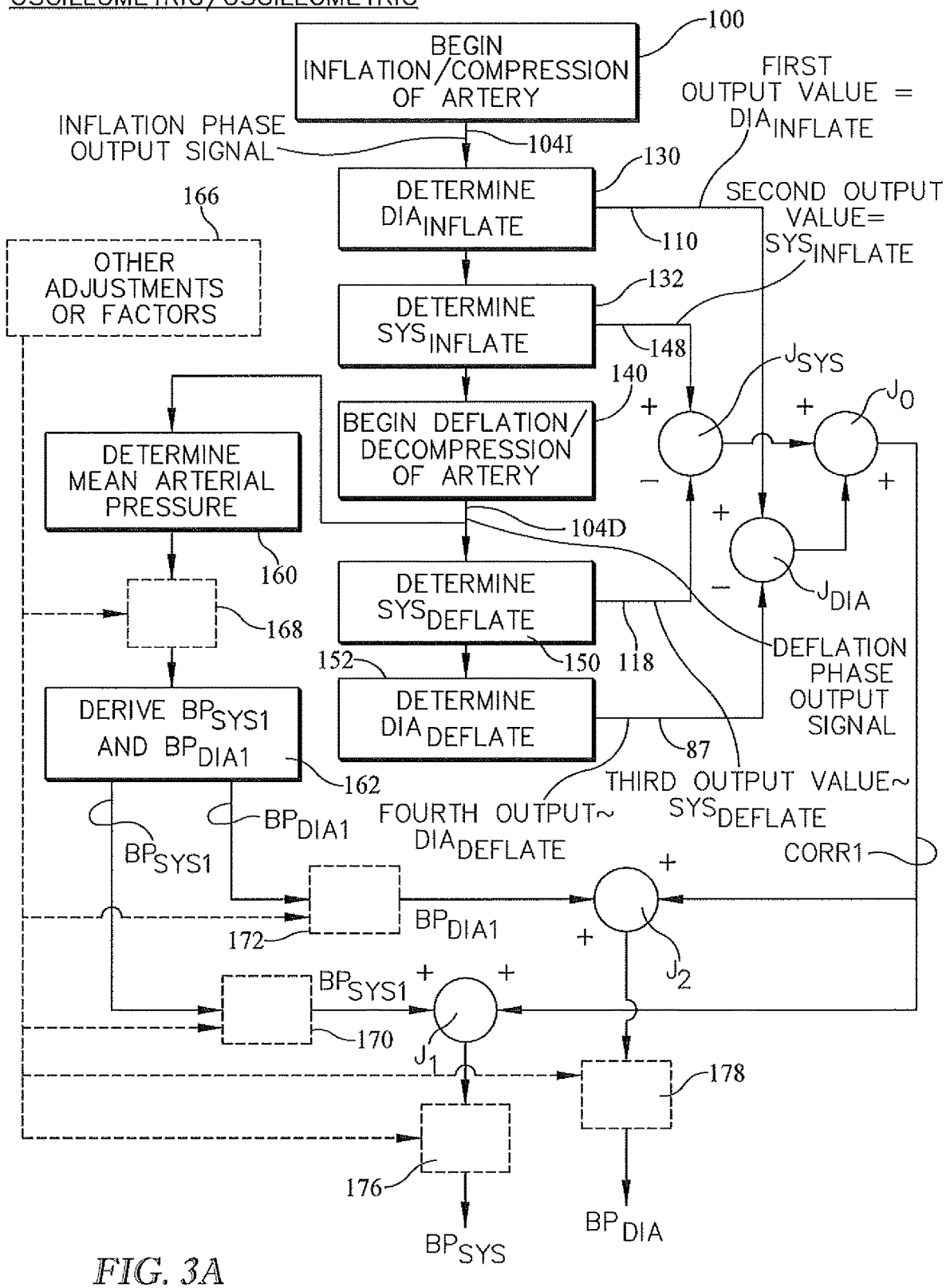
FIG. 3A is a block diagram showing operation of the blood pressure monitoring system of FIG. 1 in which the primary system employs pressure readings from the deflation phase of a blood pressure cuff and in which a single correction for arterial compliance is applied equally to both a systolic and a diastolic value obtained from the primary system.
Figure 3B:
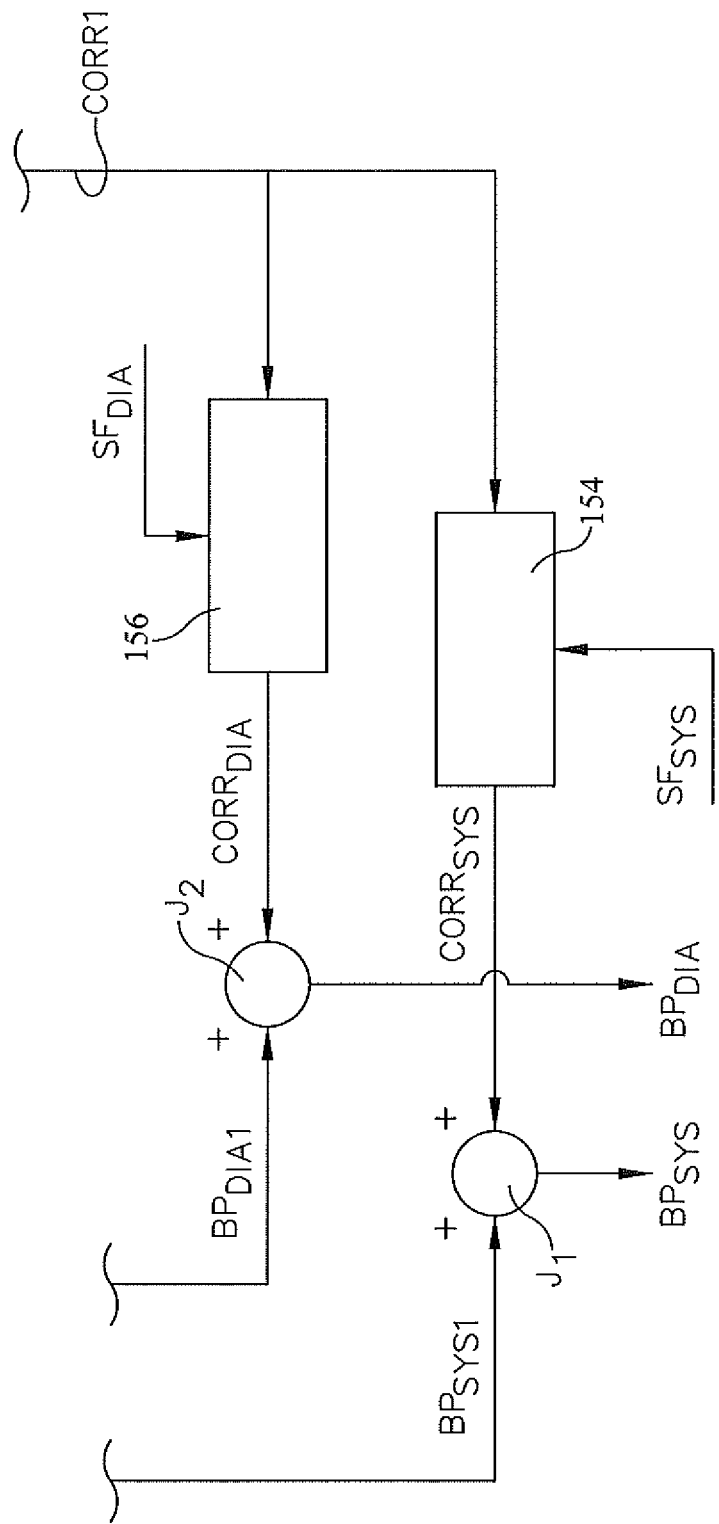
FIG. 3B is a portion of a block diagram showing a modification to the method of FIG. 3A in which different corrections for arterial compliance are applied to the systolic and a diastolic values obtained from the primary system.
Figure 3C:
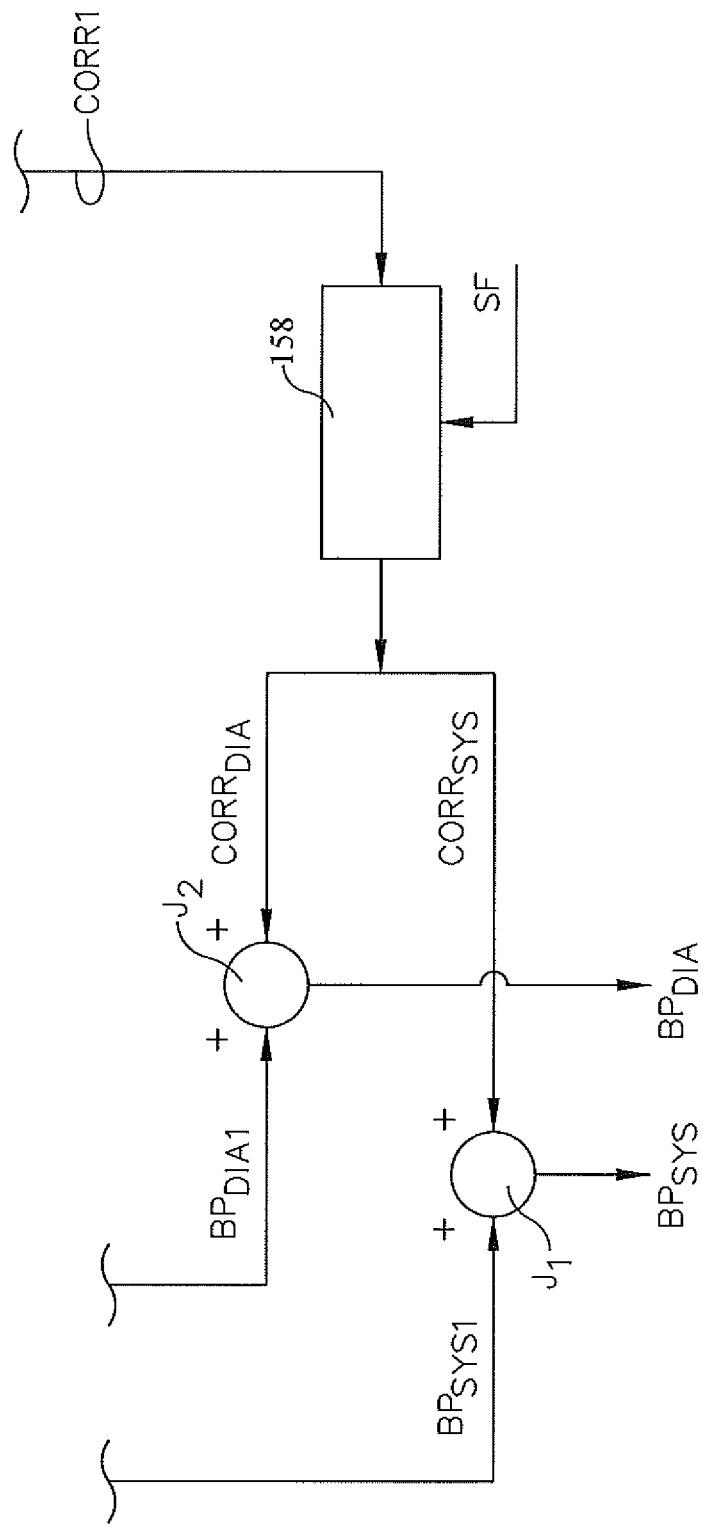
FIG. 3C is a portion of a block diagram showing a modification to the method of FIG. 3A in which a single, modified correction for arterial compliance is applied to both the systolic and diastolic values obtained from the primary system.
Figure 4:
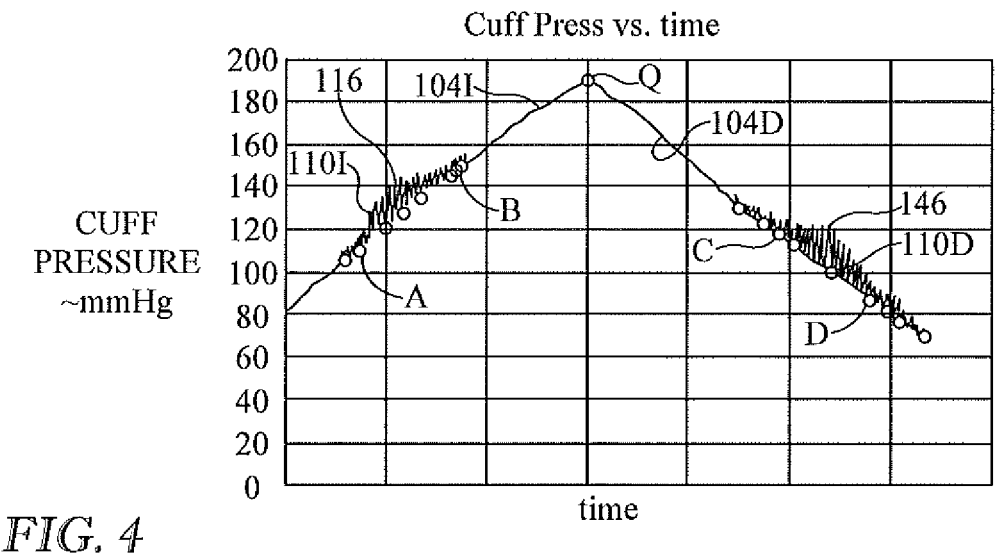
FIG. 4 is an illustrative graph showing cuff pressure vs. time of the inflation and deflation phases of a blood pressure cuff.
Figure 5:
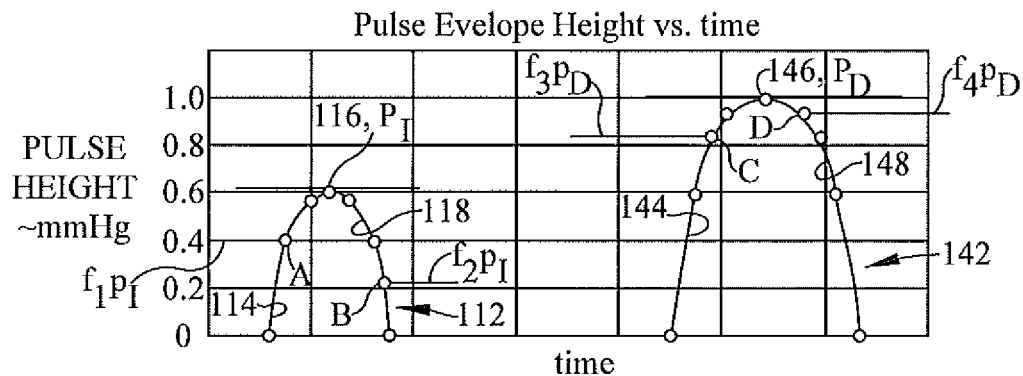
FIG. 5 is an illustrative graph showing the inflation and deflation phase pulse envelopes of FIG. 4 vs. time.
Figure 6:
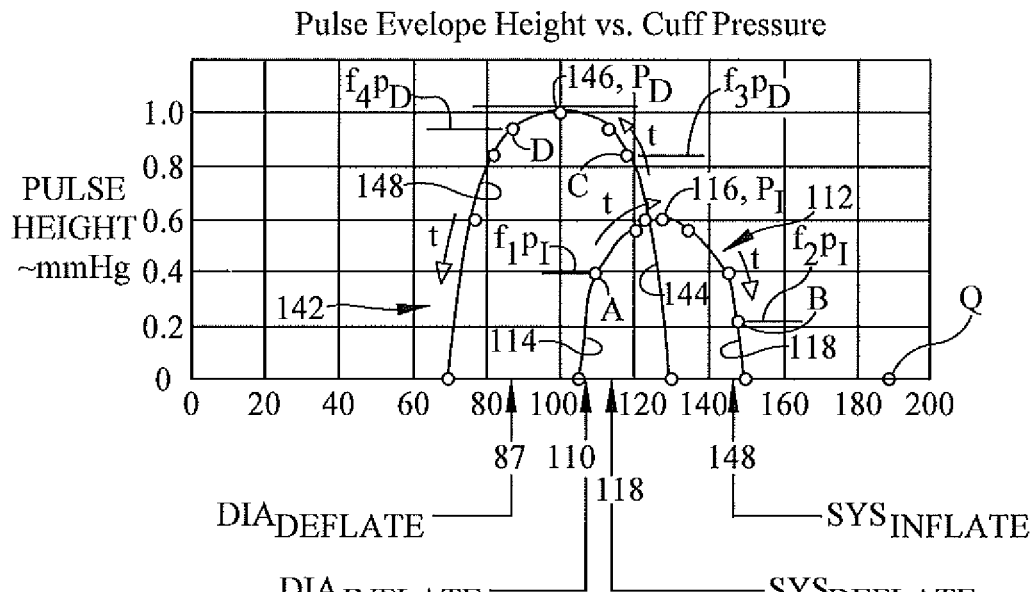
FIG. 6 is an illustrative graph showing the inflation and deflation phase pulse envelopes of FIG. 4 vs. cuff pressure.

Referring additionally to FIGS. 3-6, in practice a user presses a START button on the user interface to take a blood pressure reading. In response, at block 100 controller 56 turns on pump 34 to begin the inflation phase of operation. The pump inflates the cuff with air thereby applying compression to an artery of the subject. As the compression intensifies, the artery collapses and becomes occluded. During the inflation phase, transducer 50 receives an inflation phase pressure input signal 102I (depicted in FIG. 2) associated with the progressively compressed artery. The transducer generates an inflation phase output signal 104I, such as an electrical signal, based on the received inflation phase input signal 102I. Inflation phase output signal 104I is conveyed to processor 64. As seen in FIGS. 4-5, as the cuff pressure increases the inflation phase output signal exhibits small amplitude oscillations or pulses 110I such as those mentioned previously in connection with the deflation phase of oscillometric blood pressure determinations. In FIG. 4 the pulses are magnified for the sake of clarity. The inflation phase oscillations begin before the time the artery begins to collapse. As cuff pressure increases the oscillations increase in amplitude to a peak amplitude, and then decrease in amplitude and dematerialize. As seen in FIGS. 5-6 the inflation phase output signal defines an inflation phase pulse envelope 112 having an ascending side 114, a peak pulse amplitude 116 (also designated as $P_I$) and a descending side 118.

At blocks 130 and 132 the processor executes instructions from corrective instruction set 72 to determine first and second output values, $DIA_{INFLATE}$ and $SYS_{INFLATE}$, based on inflation phase output signal 104I. The processor may also execute instructions from the corrective instruction set which carry out ancillary tasks such as building the inflation phase pulse envelope. The first output value, $DIA_{INFLATE}$, (point A on the graphs) is the cuff pressure corresponding to the inflation phase pulse envelope height which is a first fraction $f_1$ of the peak height of pulse envelope 112, taken on the ascending side of the envelope. The second output value, $SYS_{INFLATE}$, (point B on the graphs) is the cuff pressure corresponding to a pulse envelope height which is a second fraction $f_2$ of the peak height of the inflation phase pulse envelope, taken on the descending side of the envelope. The first and second fractions need not be equal to each other. $DIA_{INFLATE}$ is a diastolic blood pressure reading determined from the inflation phase. $SYS_{INFLATE}$ is a systolic blood pressure reading determined from the inflation phase.

Once the controller has caused the pump to inflate the cuff to a supra-systolic cuff pressure (point Q on FIGS. 4 and 6) operation proceeds to block 140 where controller 58 shuts off pump 64 and operates bleed valve 38 to begin the deflation phase, thereby allowing the artery to return to its normal, pre-occluded state.

During the deflation phase, pressure transducer 50 receives a deflation phase pressure input signal 102D (depicted in FIG. 2) associated with the progressively decompressed artery. The transducer generates a deflation phase output signal 104D, such as an electrical signal, based on the received deflation phase input signal 102D. The deflation phase output signal 104D is conveyed to processor 64. As seen in FIGS. 4-5, as cuff pressure, and therefore pressure on the artery is decreased, the deflation phase output signal exhibits small amplitude oscillations or pulses 110D. In FIG. 4 the pulses are magnified for the sake of clarity, and the relative overall rates of the inflation phase pressure rise and the deflation phase pressure decay are not necessarily the relative rates employed in practice. As cuff pressure decreases the deflation phase oscillations increase in amplitude to a peak amplitude, and then decrease in amplitude and vanish. As seen in FIGS. 5-6, the deflation phase signal defines a deflation phase pulse envelope 142 having an ascending side 144, a peak pulse amplitude 146 (also designated as $P_D$) and a descending side 148.

At blocks 150 and 152 the processor executes instructions from corrective instruction set 72 to determine third and fourth output values $SYS_{DEFLATE}$, $DIA_{DEFLATE}$ based on deflation phase output signal 104D. The processor may also execute instructions from the corrective instruction set which carry out ancillary tasks such as building the deflation phase pulse envelope. The third output value, $SYS_{DEFLATE}$, (point C on the graphs) is the cuff pressure corresponding to the deflation phase pulse envelope height which is a third fraction $f_3$ of the peak height of deflation phase pulse envelope 110D, taken on the ascending side of the envelope. The fourth output value, $DIA_{DEFLATE}$, (point D on the graphs) is the cuff pressure corresponding to the deflation phase pulse envelope height which is a fourth fraction $f_4$ of the peak height of the deflation phase pulse envelope, taken on the descending side of the envelope. The third and fourth fractions need not be equal to each other, nor do either of them need to be the same as the first and/or second fractions described above in connection with the inflation phase. $SYS_{DEFLATE}$ is a systolic blood pressure reading determined from the deflation phase. $DIA_{DEFLATE}$ is a diastolic blood pressure reading determined from the deflation phase output signal 104D.

Summing junction $J_{SYS}$ subtracts the third output value ($SYS_{DEFLATE}$) from the second output value ($SYS_{INFLATE}$) and passes the result ($SYS_{INFLATE} - SYS_{DEFLATE}$) to summing junction $J_0$. Summing junction $J_{DIA}$ subtracts the fourth output value ($DIA_{DEFLATE}$) from the first output value ($DIA_{INFLATE}$) and passes the result ($DIA_{INFLATE} - DIA_{DEFLATE}$) to summing junction $J_0$. Summing junction $J_0$ adds the outputs of summing junctions $J_{SYS}$ and $J_{DIA}$ thereby establishing a correction CORR1 for arterial compliance as a function of the first, second, third, and fourth intra-arterial pressures as set forth below:

$$CORR1 = (SYS_{INFLATE} - SYS_{DEFLATE}) + (DIA_{INFLATE} - DIA_{DEFLATE}).$$

By way of example, if the first, second, third and fourth values are 110, 148, 118 and 87 mm Hg respectively as in the graphs of FIGS. 4-6, the correction is:

$$CORR1 = (148-118) + (110-87) = 30+23 = 53.$$

FIG. 3B shows a variant of the method just described in which CORR1 is modified. The modification may be, but is not limited to, a multiplicative scaling factor. At block 154, CORR1 is modified by $SF_{SYS}$ to yield correction $CORR_{SYS}$. At block 156, CORR1 is modified by $SF_{DIA}$ to yield correction $CORR_{DIA}$. By way of example, if $SF_{SYS}$ and $SF_{DIA}$ are multiplicative scaling factors having values of 0.8 and 0.7 respectively, and if the value of CORR1 is 53 as in the above example, then:

$$CORR_{SYS} = (0.8)(53) = 42, \text{ and}$$

$$CORR_{DIA} = (0.7)(53) = 37.$$

FIG. 3C shows a different modification in which a common modifier SF is applied to CORR1 to yield $CORR_{SYS}$ and $CORR_{DIA}$.

In the foregoing description the inflation phase and the generation of inflation phase output signal 104I used to determine the correction precedes the deflation phase and the generation of deflation phase output signal 104D used to determine the correction. However the described sequence can be reversed so that the deflation phase and the generation of the deflation phase output signal 104D precedes the inflation phase and the generation of the inflation phase output signal 104I. Such a sequence of actions would, of course, involve a preparatory inflation prior to the deflation and generation of the deflation phase output signal and also a re-inflation in order to generate the inflation phase output signal. In addition, and irrespective of the order of blocks 100 and 140, the analysis and calculations beginning at blocks 130, 132, 150, 152 can be deferred until both the inflation phase and deflation phase pulse envelopes have been established.

As already noted, blood pressure monitoring system 20 also includes a primary system 22 for determining a first blood pressure. As also noted previously certain components may be shared between the primary and corrective systems while other elements are dedicated to one system or the other. In the example architecture of FIG. 1 the shared components include the occlusion and sensing module (cuff 32, pump 34, tube 36, bleed valve 38 and sensor array 50) and processor 64. In an alternative example architecture shown in FIG. 7 the shared components include the occlusion and sensing module, except for the sensor array, and the processor. In yet another embodiment, not illustrated, the primary and corrective systems each include a dedicated processor.

Figure 7:
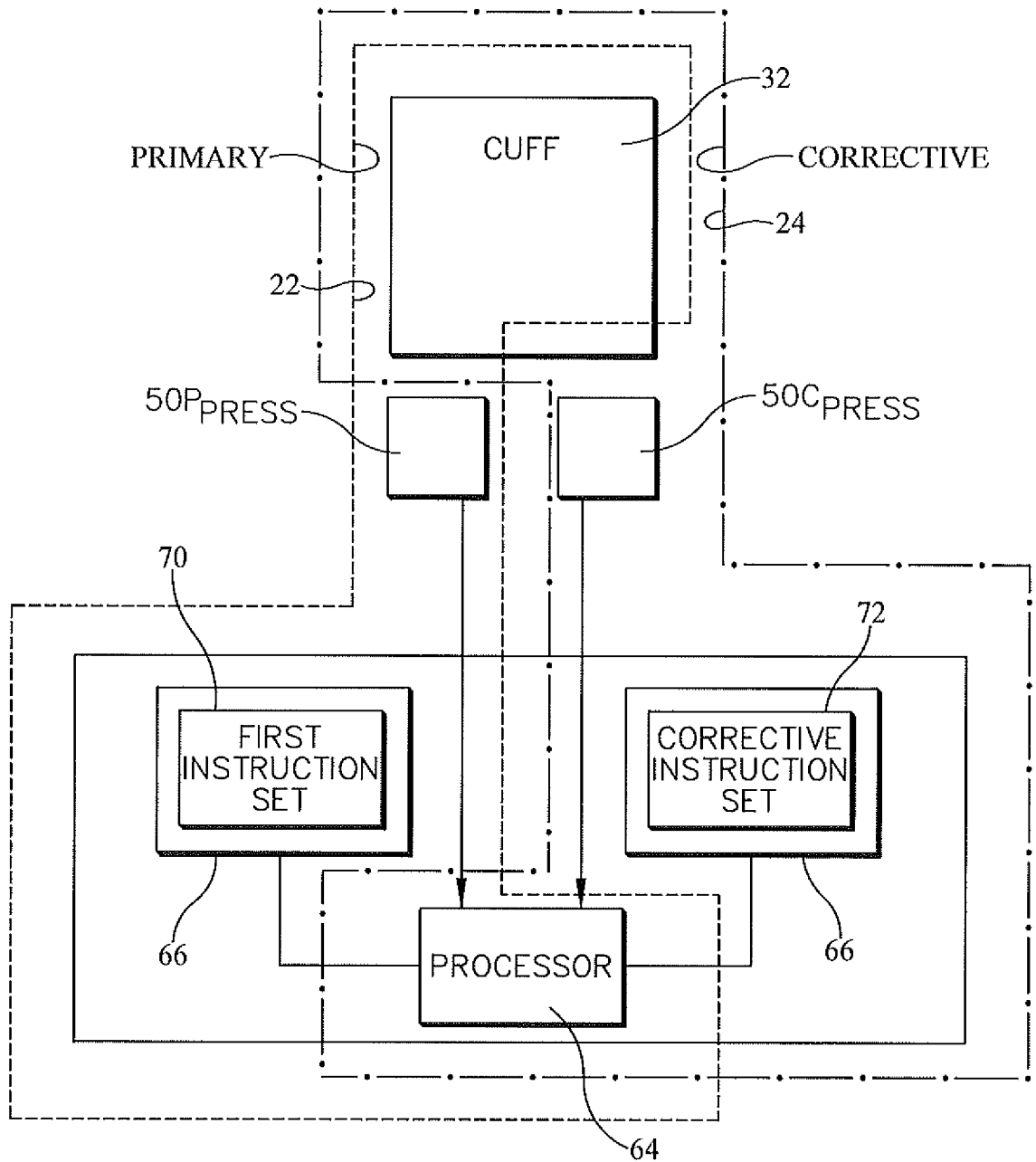
FIG. 7 is a diagram similar to that of FIG. 1 but in which the primary and corrective systems do not share a sensor array.

In the architecture of FIG. 7 the sensor array includes a primary sensor array, represented by a single sensor $50P_{PRESS}$ dedicated to the primary system, and a corrective sensor array represented by a single sensor $50C_{PRESS}$ dedicated to the corrective system. The primary and corrective sensor arrays can be thought of as first and second subsets of a larger sensor array. In one example sensor $50C_{PRESS}$ is a sensor designed to follow the high frequency oscillations 110I, 110D with high fidelity while sensor $50P_{PRESS}$ could be a less responsive, but also less expensive sensor. The block diagram of FIG. 3A is applicable to the dedicated sensor architecture of FIG. 7 with the understanding that output signal 104D entering block 150 is from the corrective sensor and output signal 104D entering block 160 (which signal is not shown separately) is from the primary sensor.

Figure 10:
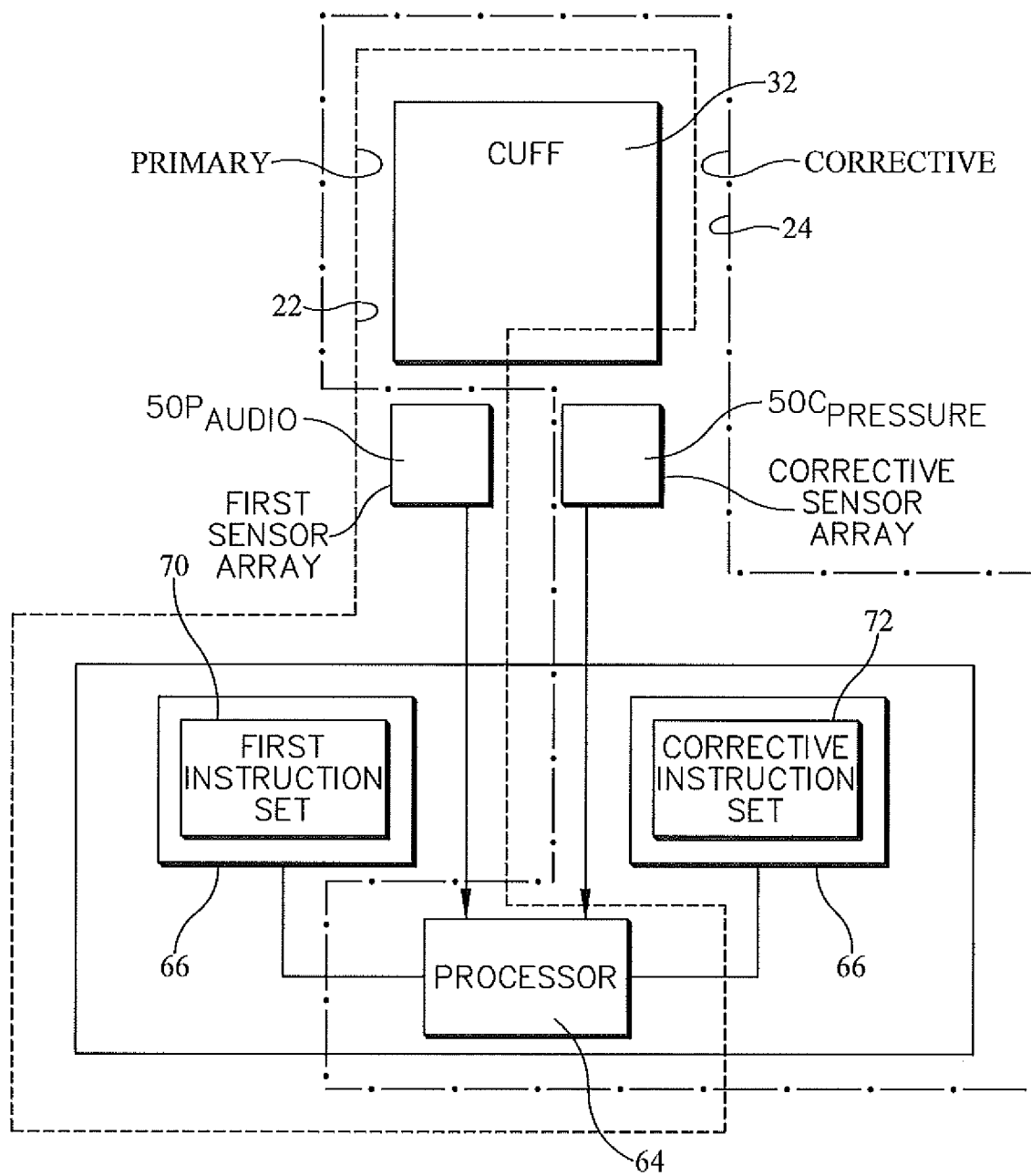
FIG. 10 is a diagram of the architecture of a blood pressure monitoring system which includes an auscultatory primary system and an oscillometric corrective system.

In the system architecture diagrams of FIGS. 1, 7 and 10, the same reference numeral, 66, signifies the memory for both primary instruction set 70 and corrective instruction set 72, correctly suggesting that the hardware or other physical structure corresponding to the memory is shared between the primary and corrective systems. However the primary and corrective systems may instead each have their own dedicated memory physical structure. Nevertheless, even if the memory physical structure is shared, the primary instruction set is for the primary system while the corrective instruction set is for the corrective system, with the possible exception of a limit case described below in which identical primary and corrective instructions are stored in a common memory locations.

Primary system 24 determines a first blood pressure, i.e. a blood pressure which does not account for arterial compliance and to which an arterial compliance correction such as correction CORR1 can be applied. In the embodiments of FIGS. 1 and 7 the first blood pressure, like the correction, is determined oscillometrically. At block 160 of FIG. 3A the primary system employs deflation phase output signal 104D to determine mean arterial pressure. Disregarding, for the moment, the diagram blocks and connections depicted with dashed lines, the method proceeds to block 162 where the primary system derives a first blood pressure based on the mean arterial pressure. The first blood pressure is a value pair signifying systolic and diastolic blood pressure $BP_{SYS1}$, $BP_{DIA1}$. The systolic pressure may be derived in the manner already described, i.e. the cuff pressure corresponding to the deflation phase pulse envelope height, which is a fraction of the peak height of deflation phase pulse envelope 110D, and which is taken on the ascending side of the envelope, is considered to be the systolic pressure. Similarly, the cuff pressure corresponding to the deflation phase pulse envelope height, which is a fraction (not necessarily the same fraction) of the peak height of the deflation phase pulse envelope, and which is taken on the descending side of the envelope, is considered to be the diastolic pressure.

Figure 8:
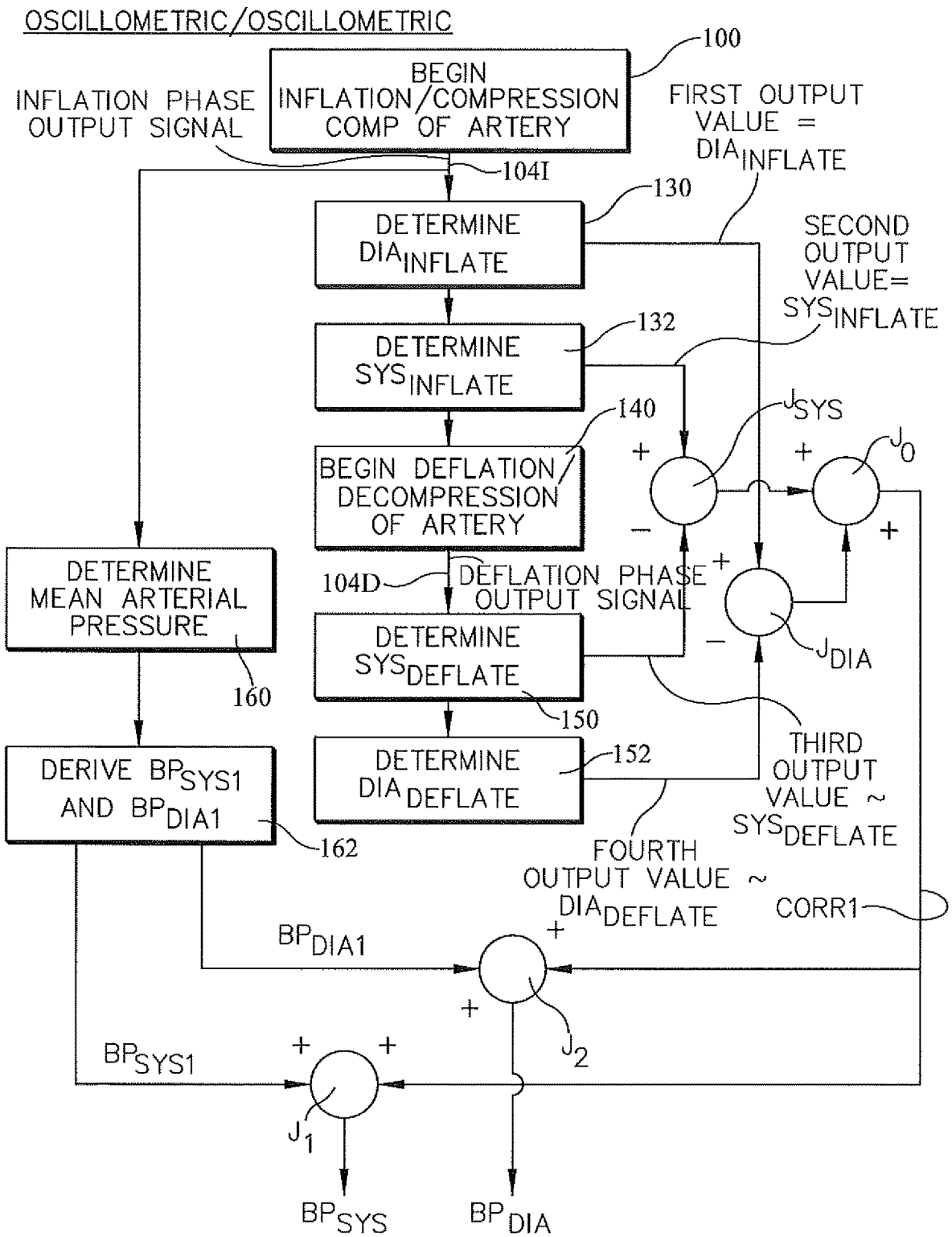
FIG. 8 is a block diagram similar to that of FIG. 3A showing operation of the blood pressure monitoring system of FIG. 1 in which the primary system employs pressure readings from an inflation phase of a blood pressure cuff.
Figure 11:
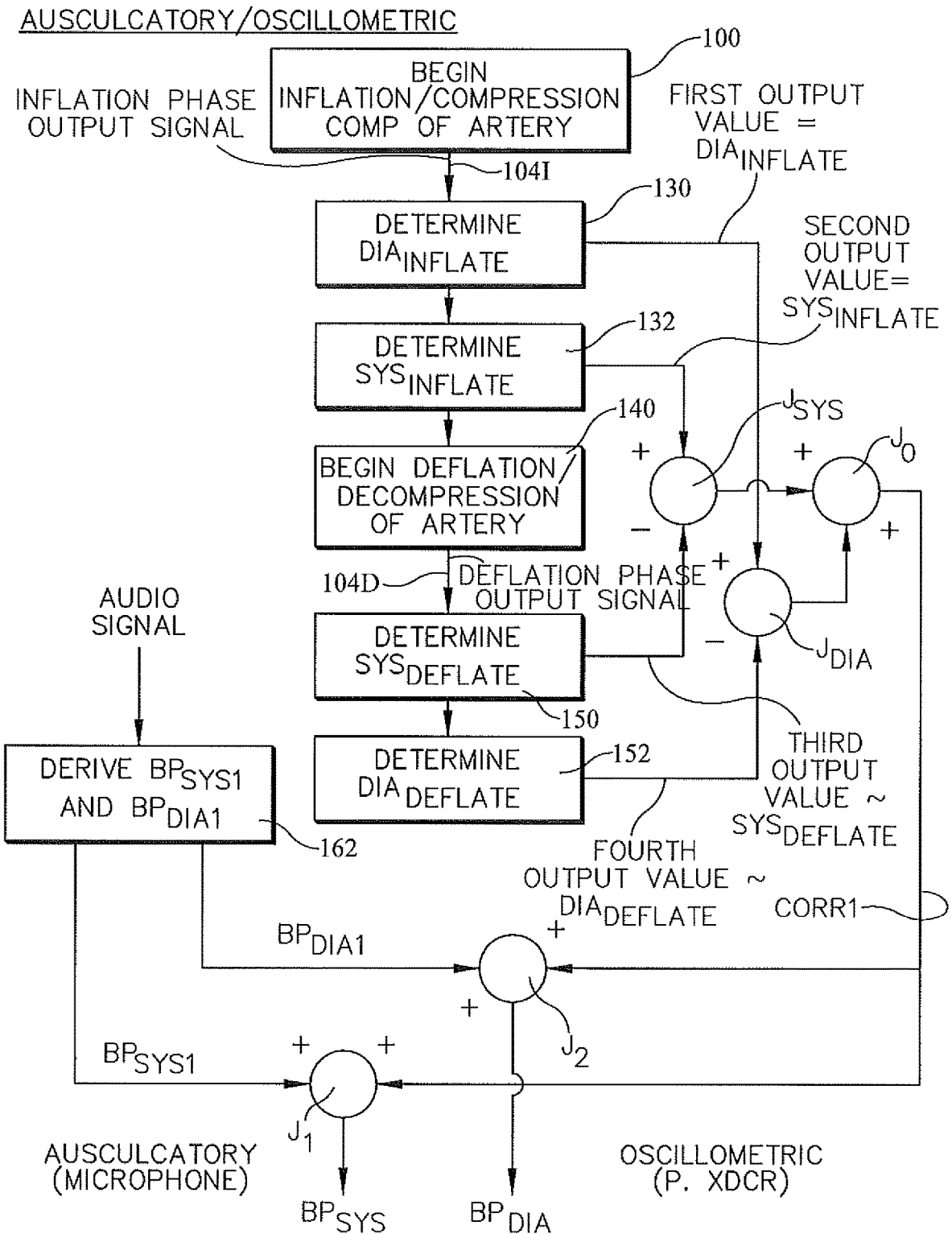
FIG. 11 is a block diagram showing operation of the blood pressure monitoring system of FIG. 10.

At summing junction $J_1$ the processor adds correction CORR1, which may be a positive or negative number, to $BP_{SYS1}$ to obtain a systolic blood pressure value $BP_{SYS}$ corrected for the effects of arterial compliance. At summing junction $J_2$ the processor adds correction CORR1 to $BP_{DIA1}$ to obtain a diastolic blood pressure value $BP_{DIA}$ corrected for the effects of arterial compliance. The signals corresponding to corrected blood pressure values are a value pair $BP_{SYS}$ and $BP_{DIA}$ output from summing junctions $J_1$ and $J_2$ to a destination such as display 56 of FIG. 2. Although FIG. 3A and the diagrams of FIGS. 8 and 11 show the correction being applied to both the systolic and diastolic values of the first blood pressure, the correction can instead be applied to only the systolic value or only the diastolic value. By way of example, if $BP_{SYS1}$=112, $BP_{DIA1}$=73, and CORR1=53 (as determined in a previous example of the corrective system) and if it is desired to apply the correction to both the systolic and diastolic first blood pressure values, then:

$$BP_{SYS}=112+53=165, \text{ and}$$

$$BP_{DIA}=73+53=126.$$

In two other variants, CORR1 is modified to yield a modified arterial compliance correction $CORR_{DIA}$ and/or $CORR_{SYS}$ as described above and as seen in either FIG. 3B, which shows different systolic and diastolic corrections, or FIG. 3C which shows a common correction.

Referring now to the blocks and connections depicted with dashed lines in FIG. 3A, an adjustment or adjustments other than the adjustment CORR1 for arterial compliance may also be applied to the first blood pressure. Such adjustments are shown at block 166. In one variant, adjustments are applied at block 168 to the estimated mean arterial pressure, in which case the derivation of $BP_{SYS1}$ and $BP_{DIA1}$ at block 162 reflects the adjustment from block 166. In another variant the adjustments are instead applied to $BP_{SYS1}$ at block 170 and/or to $BP_{DIA1}$ at block 172. In yet another variant the adjustment or adjustments are applied at blocks 176 and/or 178. Blocks 168, 170, 172, 176 and 178 as well as the connections from block 166 to those blocks are depicted with dashed lines to signify that these other adjustments may or may not exist, and if they do exist can be applied at different points in the method. The adjustments are also applicable to the methods of FIGS. 3B and 3C.

FIG. 8 shows an alternative in which the MAP and the oscillometrically determined first blood pressure are based on the inflation phase output signal 104I instead of on deflation phase output signal 104D. The inflation phase based system can use shared or dedicated sensors as already described in connection with the deflation based approach. The possibility of including adjustments from block 166 at blocks 168, or at blocks 170 and/or 172, or at blocks 176 and/or 178, as described in connection with FIG. 3A, also applies to the method of FIG. 8. The variations of FIGS. 3B and 3C also apply to FIG. 8.

In the architectures of both FIGS. 1 and 7, the primary system and the corrective system each have their own instruction set, first instruction set so that the primary system can determine the first blood pressure 70, and corrective instruction set 72 so that the corrective system can determine the correction. However this does not preclude the possibility of some overlap between the instruction sets. For example the derivation of the first blood pressure value pair $BP_{SYS1}$ and $BP_{DIA1}$ from mean arterial pressure at block 162 of FIG. 3A could use the same instructions as are used to determine $SYS_{DEFLATE}$ and $DIA_{DEFLATE}$ at blocks 150, and 152. To the extent that some of the instructions are common to both instruction sets, those instructions can be stored in different memory locations or can be stored in common memory locations as would be the case for instructions in a subroutine called by the processor. In the limit case of identical primary and corrective instructions stored in a common memory locations the instructions can be considered to be shared instructions or can be considered to be dedicated instructions.

Figure 9:
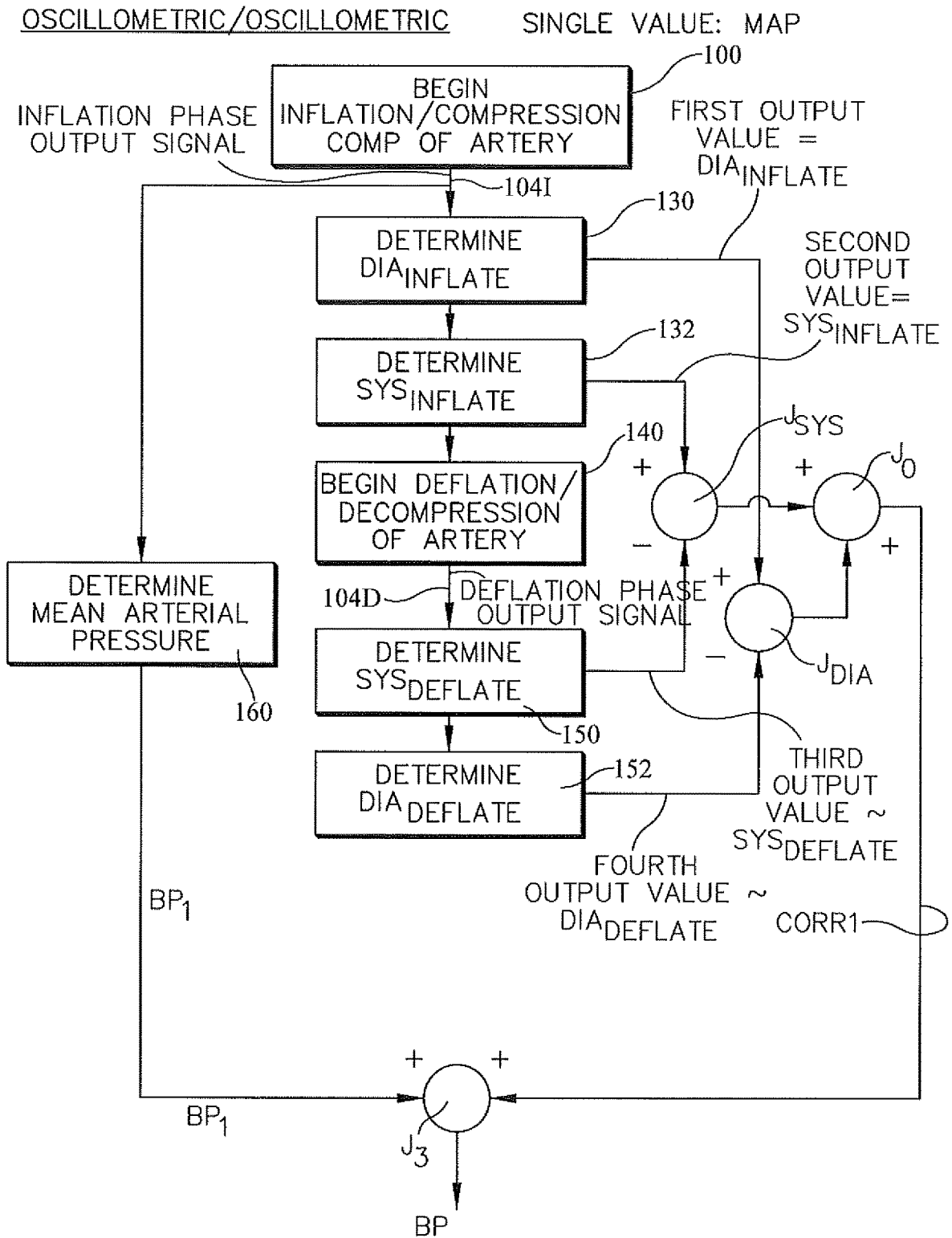
FIG. 9 is a block diagram similar to that of FIGS. 3A and 8 in which the blood pressure reading is a single value corresponding to mean arterial pressure.

FIG. 9 is a block diagram similar to that of FIGS. 3A and 8 except that the first blood pressure is a single value $BP_1$ rather than a value pair. $BP_1$ is the mean arterial pressure from block 160. Correction CORR1 is a correction to the mean arterial pressure, and the corrected blood pressure value BP is a corrected mean arterial blood pressure value. FIG. 9 shows the use of deflation phase output signal 104D but could instead use inflation phase output signal 104I, similar to the arrangement of FIG. 8. Moreover, shared or dedicated sensors can be used as in FIGS. 1 and 7 respectively. Adjustments for effects other than arterial compliance, such as those of block 166 of FIG. 3A, may be applied to $BP_1$ or BP. A modifier such as SF of FIG. 3C may also be applied.

FIG. 10 is a system architecture diagram similar to those of FIGS. 1 and 7. FIG. 11 is a block diagram similar to that of FIGS. 3A, 8 and 9. However FIGS. 10-11 show a blood pressure monitoring system in which the primary system 22 is an ausculcatory system. The corrective system 24, like that of FIGS. 3, 8, and 9, is an oscillometric system. Hence, the blood pressure monitoring system of FIGS. 10-11 is referred to as an ausculcatory/oscillometric system, abbreviated A/O. The ausculcatory primary system includes cuff 32 but relies on an audio sensor $50P_{AUDIO}$ to discern the K-sounds rather than relying on a pressure sensor such as sensor $50C_{PRESS}$ of FIG. 7, to sense the oscillations that make up the pulse envelope. The architectural diagram is analogous to that of FIG. 7 in that first sensor array, which comprises one or more audio sensors, $50P_{AUDIO}$ is part of primary system 22 and corrective sensor array $50C_{PRESS}$ is part of the oscillometric corrective system 24. The block diagram of FIG. 11 is similar to that of FIGS. 3A, 8 and 9 except that the derivation of $BP_{SYS1}$ and $BP_{DIA1}$ at block 166 is based on one or more audio signals rather than one or more pressure signals. The first instruction set 70 is configured to determine the first blood pressure value from signals generated by audio sensor $50P_{AUDIO}$. As with the O/O method, corrective instruction set 72 is configured to determine the correction from signals generated by pressure sensor $50C_{PRESS}$. Adjustments for effects other than arterial compliance, such as those of block 166 of FIG. 3A, may be applied to one or both of the outputs of block 162 or to one or both of the outputs of summing junctions $J_1$, $J_2$. Modifiers such as $SF_{SYS}$ and $SF_{DIA}$ of FIG. 3B or SF of FIG. 3C may also be applied.

The A/O primary and corrective systems do not share a sensor. However the other variations already described in connection with the O/O system are applicable to the A/O system. In particular, the A/O system can rely on audio information from the inflation phase and can be used to generate MAP, or $BP_{SYS}$ and $BP_{DIA}$, or MAP and $BP_{SYS}$ and $BP_{DIA}$.

In general, the systems for correcting a blood pressure reading for the effects of arterial compliance can be configured in at least the ways shown in tables 1 and 2 below. In the case of cuff based systems the inflation and deflation of the cuff must, of course, be slow enough and steady enough to yield accurate readings.

TABLE 1

| Primary System | Corrective System | First (primary) BP Determined from | Sensor Array |
|---|---|---|---|
| Oscillometric | Oscillometric | Deflation phase | Shared |
| Oscillometric | Oscillometric | Deflation phase | Dedicated |
| Oscillometric | Oscillometric | Inflation phase | Shared |
| Oscillometric | Oscillometric | Inflation phase | Dedicated |
| Ausculcatory | Oscillometric | Deflation phase | Dedicated |
| Ausculcatory | Oscillometric | Inflation phase | Dedicated |
| Cuffless | Oscillometric | — | Dedicated |
| Cuffless | Oscillometric | — | Dedicated |

TABLE 2

| Primary System | Corrective System | First (primary) BP Determined from | Sensor Array |
|---|---|---|---|
| Ausculcatory | Ausculcatory | Deflation phase | Shared |
| Ausculcatory | Ausculcatory | Deflation phase | Dedicated |
| Ausculcatory | Ausculcatory | Inflation phase | Shared |
| Ausculcatory | Ausculcatory | Inflation phase | Dedicated |
| Oscillometric | Ausculcatory | Deflation phase | Dedicated |
| Oscillometric | Ausculcatory | Inflation phase | Dedicated |
| Cuffless | Ausculcatory | — | Dedicated |
| Cuffless | Ausculcatory | — | Dedicated |

As already noted, the above systems and method can be used to determine, and to output to display 56, any combination of MAP, $PB_{SYS}$ and $BP_{DIA}$, although in some algorithms knowledge of MAP is a prerequisite to determining $BP_{SYS}$ and $BP_{DIA}$.

Figure 12:
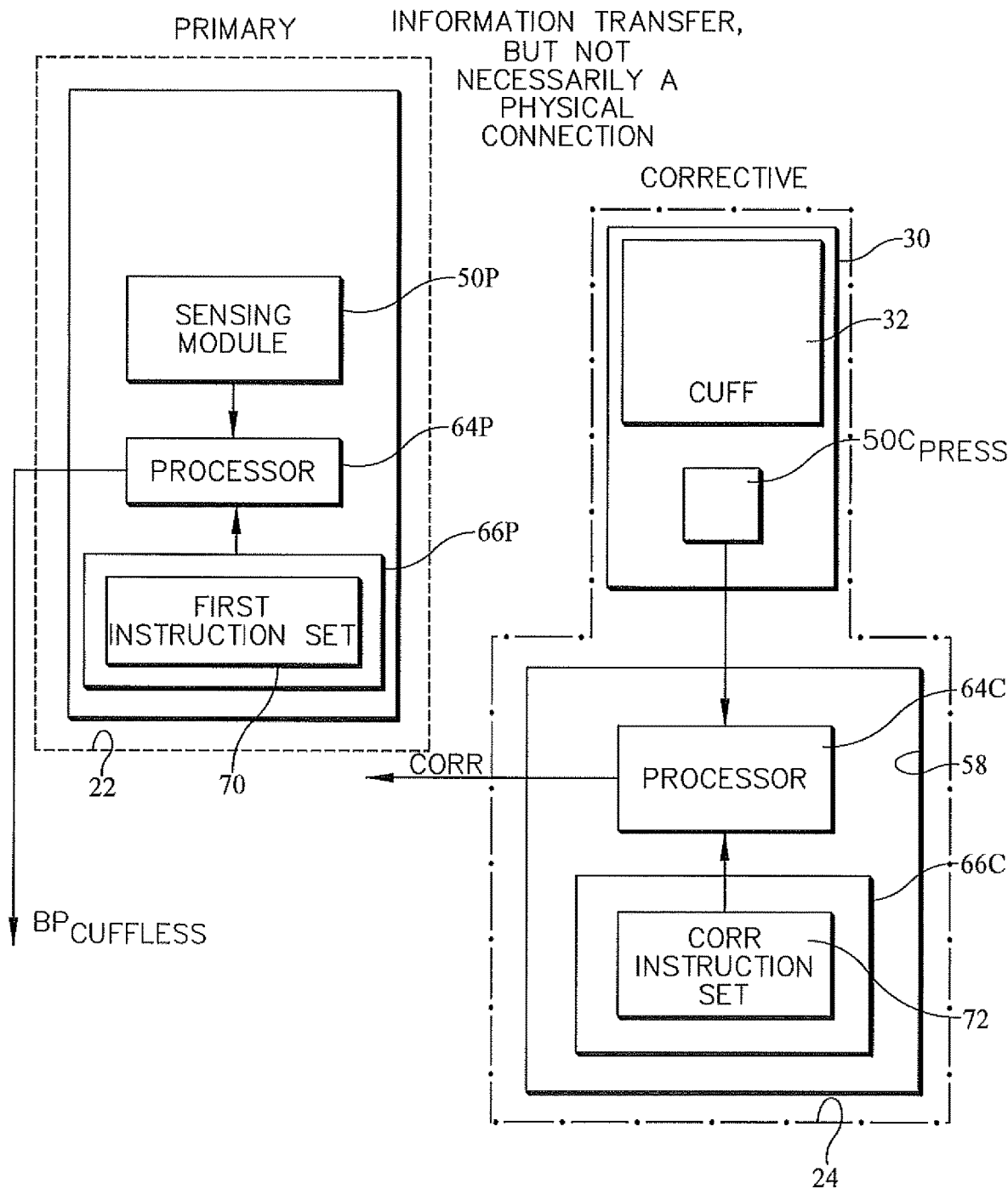
FIG. 12 is a diagram of the architecture of a blood pressure monitoring system which includes a cuffless primary system and an oscillometric corrective system.
Figure 13:
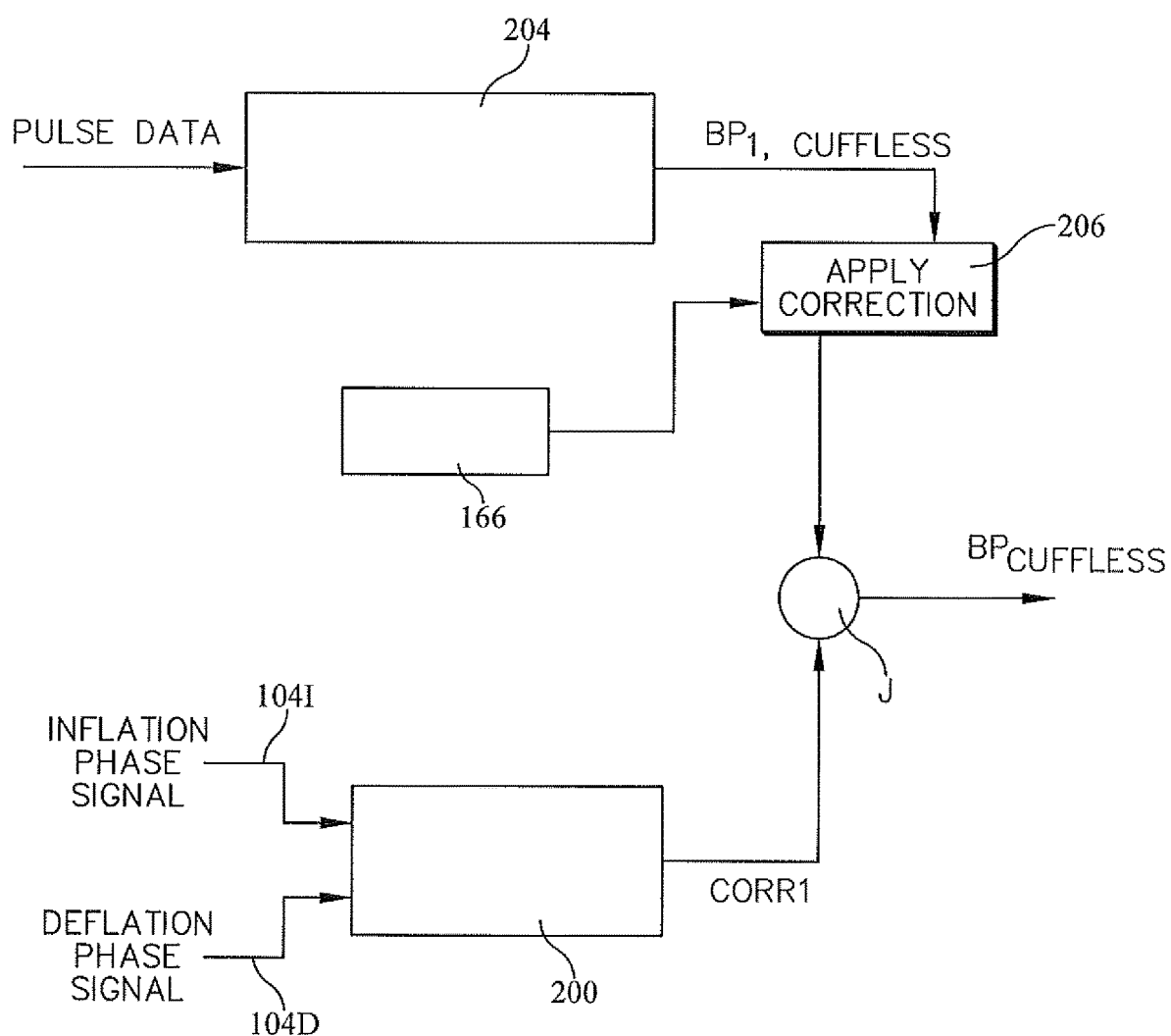
FIG. 13 is a block diagram showing operation of the blood pressure monitoring system of FIG. 12.

FIG. 12 shows the architecture of a blood pressure monitoring system 20 in which the primary system 22 is a cuffless system, such as one that bases blood pressure determinations on pulse transit time (PTT) and the corrective system 24 is an oscillometric system. FIG. 13 is a block diagram of the operation of the system of FIG. 12.

Referring first to FIG. 12, the corrective oscillometric system 24 employs a cuff 32 and a pressure sensor $50C_{PRESS}$ to sense intra-arterial pressure, a corrective instruction set 72 and a processor 64C. The cuffless primary system 22 includes a sensing module 50P for pulse sensing and a processor 64P for converting the sensed pulses to a single valued first blood pressure (e.g. MAP) or a two-valued first blood pressure (e.g. systolic and diastolic).

Referring additionally to FIG. 13, at block 200 processor 64C executes corrective instruction set 72 to determine a correction CORR1 for arterial compliance. At block 204 processor 64P executes primary instruction set 70 to determine the first blood pressure $BP_{1,CUFFLESS}$ as a function of the sensed pulses. At block 206 processor 64P applies correction CORR1 to $BP_{1,CUFFLESS}$ to arrive at $BP_{CUFFLESS}$. As with other embodiments the determination of the first blood pressure may involve the application of adjustment factors from block 166 other than correction CORR1. The corrections, if any, from block 166 may be applied at block 206 prior to summing junction J as shown, or may be applied after summing junction J. The modifications of FIGS. 3B and 3C are also applicable to the method of FIG. 13.

Conveyance of correction CORR1 or its variants from processor 64C to processor 64P may be carried out automatically by way of a physical connection or wirelessly.

Alternatively the conveyance can be carried out manually, for example by a caregiver reading the value of CORR1 from a display and then providing that correction to the primary system by way of, for example, a keypad.

In the system represented by FIGS. 12-13, CORR1 may be a calibration which is applied periodically to the primary system rather than a more continuously applied correction, in which case manual conveyance of the correction from processor 64C to processor 64P may be satisfactory. Alternatively, the correction may be applied more continuously, if desired, in which case automatic conveyance of the correction from processor 64C to processor 64P as described above may be more suitable.

In another embodiment, not illustrated, corrective system 24 of FIG. 12 is an ausculcatory system and the sensor array is an audio sensor or sensors $50C_{AUDIO}$ rather than pressure sensor $50C_{PRESS}$.

Although this disclosure refers to specific embodiments, it will be understood by those skilled in the art that various changes in form and detail may be made without departing from the subject matter set forth in the accompanying claims.

We claim:

1. A system for monitoring blood pressure of a subject comprising:
   a primary system for determining a first blood pressure; and
   a corrective system comprising:
      a cuff configured to be operated in 1) an inflation phase to at least partially occlude an artery of the subject and 2) a deflation phase;
      a sensor array configured to A) receive an inflation phase input signal associated with the at least partially occluded artery, B) generate an inflation phase output signal based on the received inflation phase signal, C) receive a deflation phase input signal associated with the artery, and D) generate a deflation phase output signal based on the received deflation phase signal; and
      a processor configured to a) receive the inflation phase output signal and determine therefrom first and second output values, b) receive the deflation phase output signal and determine therefrom third and fourth output values, and c) determine a correction applicable to the first blood pressure, the correction being a function of the first, second, third and fourth output values.

2. The system of claim 1 wherein the processor is configured to determine the first blood pressure based on one of the inflation phase output signal and the deflation phase output signal.

3. The system of claim 1 wherein the processor is configured to apply the correction to the first blood pressure thereby producing a corrected blood pressure value and to output a signal corresponding to the corrected blood pressure value.

4. The system of claim 3 wherein the corrected blood pressure value is a single value indicating mean arterial pressure.

5. The system of claim 3 wherein the corrected blood pressure value is a value pair signifying systolic and diastolic blood pressure.

6. The system of claim 3 wherein the first blood pressure of the subject is a value pair signifying systolic and diastolic blood pressure, and the correction is applied to only one member of the pair.

7. The system of claim 1 including a cuff controller configured to control inflation and deflation of the cuff.

8. The system of claim 1 wherein the correction is:

$$(SYS_{INFLATE} - SYS_{DEFLATE}) + (DIA_{INFLATE} - DIA_{DEFLATE}), \text{ where:}$$

$SYS_{INFLATE}$ is the second output value and indicates a systolic pressure associated with the inflation phase;
$SYS_{DEFLATE}$ is the third output value and indicates a systolic pressure associated with the deflation phase;
$DIA_{INFLATE}$ is the first output value and indicates a diastolic pressure associated with the inflation phase; and
$DIA_{DEFLATE}$ the fourth output value and indicates a diastolic pressure associated with the deflation phase.

9. The system of claim 8 wherein:
1) the inflation phase output signal defines an inflation phase pulse envelope having an ascending side, a peak pulse amplitude and a descending side and wherein:
   A) $DIA_{INFLATE}$ is cuff inflation pressure at a pulse amplitude which is a first fraction of the inflation phase peak pulse amplitude and is taken on the ascending side of the envelope;
   B) $SYS_{INFLATE}$ is cuff inflation pressure at a pulse amplitude which is a second fraction of the inflation phase peak pulse amplitude and is taken on the descending side of the envelope;
2) the deflation phase output signal defines a deflation phase pulse envelope having an ascending side, a peak pulse amplitude and a descending side and wherein:
   C) $SYS_{DEFLATE}$ is cuff inflation pressure at a pulse amplitude which is a third fraction of the deflation phase peak pulse amplitude and is taken on the ascending side of the envelope;
   D) $DIA_{DEFLATE}$ is cuff inflation pressure at a pulse amplitude which is a fourth fraction of the deflation phase peak pulse amplitude and is taken on the descending side of the envelope.

10. The system of claim 2 wherein the primary system and the corrective system share the cuff and sensor array, the primary system includes a first instruction set configured to determine the first blood pressure, and the corrective system includes a corrective instruction set configured to determine the correction.

11. The system of claim 1 wherein the primary system is an oscillometric system and the corrective system is an oscillometric system.

12. The system of claim 1 wherein the primary system is an ausculcatory system and the corrective system is an oscillometric system.

13. The system of claim 2 wherein the primary system and the corrective system share the cuff, the primary system includes a first subset of the sensors of the sensor array and a first instruction set configured to determine the first blood pressure, and the corrective system includes a second subset of the sensors of the sensor array and a corrective instruction set configured to determine the correction.

14. The system of claim 13 wherein:
   a) the first subset of the sensors of the sensor array includes an audio sensor;
   b) the first instruction set uses a signal from the audio sensor;
   c) the second subset of the sensor array includes a pressure sensor; and
   d) the corrective instruction set uses a signal from the pressure sensor.

15. The system of claim 1 wherein the correction accounts for arterial compliance.

16. The system of claim 1 wherein the primary system is a cuffless system, and the corrective system is an oscillometric system.

17. A system for correcting a first blood pressure value of a subject comprising:
   a cuff configured to be operated in 1) an inflation phase to at least partially occlude an artery of the subject and 2) a deflation phase;
   a sensor array configured to A) receive an inflation phase input signal associated with the at least partially occluded artery, B) generate an inflation phase output signal based on the received inflation phase signal, C) receive a deflation phase signal associated with the artery, and D) generate a deflation phase output signal based on the received deflation phase signal; and
   a processor configured to a) receive the inflation phase output signal and determine therefrom first and second output values, b) receive the deflation phase output signal and determine therefrom third and fourth output values, and c) determine a correction as a function of the first, second, third and fourth output values.

18. The system of claim 17 wherein the processor receives the first blood pressure value of the subject, and applies the correction to the first blood pressure value thereby producing a corrected blood pressure value.

19. The system of claim 18 wherein the first blood pressure value of the subject is a single value signifying mean arterial pressure, the correction is a correction to the mean arterial pressure, and the corrected blood pressure value is a corrected mean arterial blood pressure value.

20. The system of claim 18 wherein the first blood pressure value of the subject is a value pair signifying systolic and diastolic blood pressure, the correction is a correction to the value pair, and the corrected blood pressure value is a value pair signifying systolic and diastolic blood pressure.

21. The system of claim 18 wherein the first blood pressure value of the subject is a value pair signifying systolic and diastolic blood pressure, and the correction is applied to only one member of the pair.

22. The system of claim 17 including a cuff controller configured to control inflation and deflation of the cuff.

23. The system of claim 17 wherein the correction is:

$(SYS_{INFLATE} - SYS_{DEFLATE}) + (DIA_{INFLATE} - DIA_{DEFLATE})$, where:

$SYS_{INFLATE}$ is the second output value and indicates a systolic pressure associated with the inflation phase;
$SYS_{DEFLATE}$ is the third output value and indicates a systolic pressure associated with the deflation phase;
$DIA_{INFLATE}$ is the first output value and indicates a diastolic pressure associated with the inflation phase; and
$DIA_{DEFLATE}$ the fourth output value and indicates a diastolic pressure associated with the deflation phase.

24. The system of claim 23 wherein:
1) the inflation phase signal defines an inflation phase pulse envelope having an ascending side, a peak pulse amplitude and a descending side and wherein:
   A) $DIA_{INFLATE}$ is cuff inflation pressure at a pulse amplitude which is a first fraction of the inflation phase peak pulse amplitude and is taken on the ascending side of the envelope;
   B) $SYS_{INFLATE}$ is cuff inflation pressure at a pulse amplitude which is a second fraction of the inflation phase peak pulse amplitude and is taken on the descending side of the envelope;
2) the deflation phase signal defines a deflation phase pulse envelope having an ascending side, a peak pulse amplitude and a descending side and wherein:
   C) $SYS_{DEFLATE}$ is cuff inflation pressure at a pulse amplitude which is a third fraction of the inflation phase peak pulse amplitude and is taken on the ascending side of the envelope;
   D) $DIA_{DEFLATE}$ is cuff inflation pressure at a pulse amplitude which is a fourth fraction of the deflation phase peak pulse amplitude and is taken on the descending side of the envelope.

25. The system of claim 17 wherein the system is an oscillometric system comprising a pressure transducer.

26. The system of claim 17 wherein the correction accounts for arterial compliance.

27. A method of determining a correction to the blood pressure of a subject comprising the steps of:
   applying compression to an artery of the subject, thereby generating an inflation phase output signal, the compression being sufficient to at least partially occlude the artery;
   determining, from the inflation phase output signal, a first intra-arterial pressure and a second intra-arterial pressure associated with a compression phase pulse envelope;
   releasing the compression applied to the artery thereby generating a deflation phase output signal;
   determining, from the deflation phase output signal, a third intra-arterial pressure and a fourth intra-arterial pressure associated with a decompression phase pulse envelope;
   establishing a correction as a function of the first, second, third, and fourth intra-arterial pressures.

28. The method of claim 27 wherein the steps of applying compression and generating an inflation phase output signal which is used to determine the correction precedes the steps of releasing the compression and generating a deflation phase output signal used to determine the correction.

29. The method of claim 27 wherein the determining steps are carried out oscillometrically.

30. The method of claim 27 wherein the function of the first, second, third, and fourth intra-arterial pressures is:

$CORR1 = (SYS_{INFLATE} - SYS_{DEFLATE}) + (DIA_{INFLATE} - DIA_{DEFLATE})$ where:
CORR1 is the correction;
$SYS_{INFLATE}$ is a systolic pressure from the inflation phase pulse envelope;
$SYS_{DEFLATE}$ is a systolic pressure from the deflation phase pulse envelope;
$DIA_{INFLATE}$ is a diastolic pressure from the inflation phase pulse envelope;
$DIA_{DEFLATE}$ is a diastolic pressure from the deflation phase pulse envelope.

31. The method of claim 30 wherein $SYS_{INFLATE}$, $-SYS_{DEFLATE}$, $DIA_{INFLATE}$, and $DIA_{DEFLATE}$ are derived from mean arterial pressure.

32. The method of claim 30 wherein:
   the inflation phase pulse envelope has an ascending side, a peak pulse amplitude and a descending side;
   the deflation phase pulse envelope has an ascending side, a peak pulse amplitude and a descending side; and
   A) $DIA_{INFLATE}$ is cuff inflation pressure at a pulse envelope amplitude which is a first fraction of the inflation phase peak pulse amplitude and is taken on the ascending side of the inflation phase pulse envelope;

B) $SYS_{INFLATE}$ is cuff inflation pressure at a pulse envelope amplitude which is a second fraction of the inflation phase peak pulse amplitude and is taken on the descending side of the inflation phase pulse envelope;

C) $SYS_{DEFLATE}$ is cuff inflation pressure at a pulse envelope amplitude which is a third fraction of the deflation phase peak pulse amplitude and is taken on the ascending side of the deflation phase pulse envelope; and D) $DIA_{DEFLATE}$ is cuff inflation pressure at a pulse envelope amplitude which is a fourth fraction of the deflation phase peak pulse amplitude and is taken on the descending side of the deflation phase pulse envelope.

\* \* \* \* \*